United States Patent [19]

Wigler

[11] Patent Number: 4,866,166

[45] Date of Patent: Sep. 12, 1989

[54] BIOASSAY FOR TRANSFORMING GENES AND GENES DETECTED THEREBY

[75] Inventor: Michael Wigler, Osterhout, N.Y.

[73] Assignee: Cold Spring Harbor Laboratory, Cold Spring Harbor, N.Y.

[21] Appl. No.: 647,881

[22] Filed: Aug. 31, 1984

[51] Int. Cl.$^4$ .................. C07H 21/00; C12N 1/00; C12N 15/00

[52] U.S. Cl. .................. 536/27; 435/320; 935/9; 935/27

[58] Field of Search ........... 435/6, 253, 254, 240, 435/948, 172.3, 320; 436/501, 813; 935/9, 3, 27, 28, 31, 78; 536/27

[56] References Cited

U.S. PATENT DOCUMENTS 4,522,918  6/1985  Schlom et al. .................. 436/548 X
4,535,058  8/1985  Weinberg et al. .............. 436/813 X

OTHER PUBLICATIONS

Fasano, O. et al., *Molecular and Cellular Biology*, vol. 4, No. 9, Sep. 1984, pp. 1695–1705.
Perucho, M. et al, *Cell*, vol. 27, Dec. 1981, pp. 467–476.
Blair, D. G. et al, *Science*, vol. 218, Dec. 1982, pp. 1122–1125.

*Primary Examiner*—Johnnie R. Brown
*Assistant Examiner*—Jeremy M. Jay
*Attorney, Agent, or Firm*—Joel K. Dranove

[57] ABSTRACT

A sensitive bioassay for transforming genes based on the tumorigenicity of cotransfected NIH3T3 cells in nude mice is disclosed. Genes mcf2 and mcf3 have been detected in tissue breast cancer using this assay.

2 Claims, 5 Drawing Sheets

BIOASSAY FOR TRANSFORMING GENES AND GENES DETECTED THEREBY

BACKGROUND

The transfer of genomic DNA into HIH3T3 cells has led to the discovery that genes present in some tumor cells are capable of inducing foci of morphologically transformed NIH3T3 cells (Krontiris, T. G., et al. (1981) Proc. Natl. Acad. Sci. USA 78: 1181–1184; Murray, M. J., et al. (1981) Cell 25: 355–361; Perucho, M., et al. (1981) Cell 27: 467–476; Pulciani, S., et al. (1982) Proc. Natl. Acad. Sci. USA 79: 2845–2849; Shih, C., et al. (1979) Proc. Nat'l. Acad. Sci. USA, 76: 5714–5718). Most of the transforming genes which have been detected this way have now been identified as members of the ras gene family, either H-, K- or N-ras (Der, C., et al. (1982) Proc. Natl. Acad. Sci. USA 79: 3637–3640; Hall, A., et al. (1983) Nature 396–400; Parada, L. F., et al. (1982) Nature 297: 474–478; Pulciani, S., et al. (1982) Supra; Santos, E., et al. (1982) Nature 298: 343–347; Shimizu, K., et al. (1983b) Proc. Natl. Acad. Sci, USA 80: 2112–2116). The transforming ras genes detected by the HIH3T3 focus assay have structural gene mutations that account for their transforming activity (Reddy, E. R., et al. (1982) Nature 149–152; Tabin, C. J., et al. (1982) Nature 143–148; Taparowsky, E., et al. (1983) Cell 34: 581–586; Taparowsky, E., et al. (1982) Nature 300: 762–765; Yuasa, Y., et al. (1983) Nature 303: 775–779). Since the great majority of tumor DNAs tested fail to induce transformed foci (Krontiris, T. G., et al. (1981) Proc. Natl. Acad. Sci. USA 78: 1181–1184; Perucho, M., et al. (1981) Cell 27: 467–476; Pulciani, S., et al. (1982) Proc. Natl. Acad. Sci. USA 79: 2845–2849), it has been proposed that the focus assay has a bias for ras genes containing structural mutations. Therefore alternative assays for transforming genes present in NIH3T3 cells after DNA transfer have been sought.

SUMMARY

This invention relates to an assay system that detects oncogenes. The assay relies on the ability of transformed NIH3T3 cells to form tumors in nude mice and also incorporates methods of cotransfection (Wigler, M., et al. (1979) Cell 6: 777–785) to heighten sensitivity. In preferred embodiments of the assay, NIH 3T3 cells are co-transferred with cellular DNA and DNA capable of rendering animal cells resistant to a target chemical, the transfected NIH 3T3 cells are cultured to produce colonies resistant to the target chemical, and the colonies are injected into a mammal where appearance and growth of tumors are observed as positive indication of transforming genes in the cellular DNA. Preferably the target chemical is the antibiotic G 418 and DNA capable of rendering animal cells resistant to the target chemical is from the pKOneo plasmid. Using this assay three human transforming genes from the DNA of MCF-7, a human breast carcinoma cell line have been transferred. One of these genes is N-ras. THe other two, mcf 2 and mcf 3 appear to be unrelated to previously known transforming genes. The DNA of the transforming genes mcf 2 and mcf 3 is identified by the given restriction cleavage map. The DNA segment may be inserted into an appropriate host vector, to replicate in bacteria or yeast, for example. This DNA or RNA complementary to it may also be synthesized in vitro either chemically or biochemically in vitro or in vivo.

The DNA of the present invention may be used as a hybridization probe for oncogenes in human cancer cells. The DNA may be inserted into a suitable plasmid or other vector for this purpose. Likewise cDNA or RNA or other synthetic DNA may be used as hybridization probes.

The present invention also relates to proteins coded-for by the mcf2 and mcf3 transforming genes. These proteins or parts thereof may be expressed by cells containing the DNA or fragments thereof, or may be synthesized in vitro. The protein may be used to raise antibodies, preferably monoclonal antibodies useful for immunological detection.

The mcf2 and mcf3 genes may be used to screen for anti-cancer drugs. Thus growing cells containing the DNA or segments thereof may be observed in the presence of the drugs. Differences in amounts and kinds of protein expression, for example, may be observed.

Also protein coded by mcf2 and mcf3 transforming genes and produced in suitable hosts such as yeast or bacteria or animal cells can be used as substrate to test drugs which directly interfere with protein function.

DRAWINGS

FIG. 1 Human repeat sequences in transformants. DNAs (10 μg each) from the indicated tumors were digested with EcoR1 and analysed by Southern hybridization for the presence of human repeat sequences under conditions of high stringency. Total nick translated human DNA was used as probe. Numbers on the left are molecular weight markers in kilobases. Arrows indicate restriction endonuclease fragments with human repeat sequences which have been consistently transferred into secondary transformants.

FIG. 2: Presence of N-ras in transformants and MCF-7. Various DNAs (10 μg each) were digested with EcoR1 and analysed by Southern hybridization for the presence of the N-ras gene. The partial cDNA clone p6aI (50) was nick translated and used as probe. This probe hybridizes more strongly with the 3' EcoR1 fragment of N-ras than with the 5' EcoR1 fragment (50). Panel A: (a) NIH3T3 DNA; (b) DNA from a normal human fibroblast cell line, GM2998; (c) DNA from a human placenta; (d) DNA from MCF-7 cells; (e) DNA from the primary tumor MCF-7-1. Nitrocellulose filters were exposed for 24 hours at −70° C. with intensifying screens. Panel B: (a) DNA from primary tumor MCF-7-2; (b) DNA from primary tumor MCF-7-3; (c) DNA from primary tumor MCF-7-1; (d) DNA from secondary tumor MCF-7-1-2; (e) DNA from the secondary tumor MCF-7-1-3. The hybridizations were done at high stringency. Exposure was for 12 hours. Numbers on the right are DNA molecular weight markers in kilobases.

FIG. 3: Eco R1 restriction fragments of clones of mcf2 and mcf3. Panels A and C indicate EcoR1 inserts of independent charon 4a clones of mcf2 and mcf3, respectively. Numbers to the left refer to the λ clone designation (for example, clone λmcf2-10 or λmcf3-30B, etc.). Panels B and D indicate the composite EcoR1 restriction endonuclease map of these genes. Vertical lines indicate EcoR1 sites. The relative position of the Eco R1 fragments were determined from digests of phages with overlapping inserts. Not all such phages are shown. Ambiguity in relative position are indicated by arrows. Numbers below the fragments are their length in kb pairs. For each fragment, boxes indicate hybridization signal with total human DNA (lower box), human alu clone blur 8 (20) (middle box) or total mouse DNA (upper box). Filled in boxes indicate a strong hybridization signal, slashed boxes indicate a very weak signal and empty boxes indicate no observable hybridization signal. See FIG. 4 for typical blot hybridization data.

FIG. 4: Hybridization of λ phage clones of the mcf2 and mcf3 genes with human and mouse repetive sequences. In Panel A is shown the ethidium bromide staining pattern of a 1% agarose gel loaded with 1.5 μg of EcoR1 digests of DNA form the following λ clones: λmcf2-10, -28 and -60 (lanes a, b and c, respectively) from the secondary tumor MCF-7-2-2; λmcf-3-12A, -29 and -30B (lanes d, e and f) from the secondary tumor MCF-7-3-4; λmcf3-7A (lane h) from the human cell line MCF-7, which was isolated using an mcf3 specific probe. Lane g shows an Eco R1-Bam H1 digest of λmyc4.1.1, a cloned myc gene from mouse plasmacytoma MOPC315 (39) used as a positive control for mouse repeat sequences. The length of the inserts, indicated except for lane g, is given in kb pairs. Panel B, C and D show a Southern blot hybridization of the gel shown in panel A with nick-translated total human DNA, after two hours exposure (panel B), and with nick-translated total mouse DNA, after either four days (panel C) or two hours exposure (panel D). The hybridizations were done at high stringency (see Materials and Methods), and exposure was at −70° C. with intensifying screen.

FIG. 5 Presence of mcf2 and mcf3 genes in human DNA and DNA from transformants. DNAs (10 μg) from various sources were cleaved with EcoR1 and analyzed by the method of Southern for DNA sequences homologous to mcf3 (panel A) or mcf2 (panel B). Hybridization probes used were: the 1.9 kbp alu-free EcoR1 fragment of mcf3 and the 2.4 kbp alu-free fragment of mcf2, respectively (see FIG. 3). DNAs were as follows. Panel A: (a) NIH3T3 DNA; (b) DNA from human fibroblast cells GM2998; (c) DNA from human placenta; (d) DNA from MCF-7; (e) DNA from primary tumor MCF-7-1; (f) DNA from primary tumor MCF-7-2; (g) DNA from primary tumor MCF-7-3; (h) DNA from Hu1, a primary NIH3T3 focus transformant obtained from G. Cooper which reportedly contains a transforming gene from MCF-7; (i) DNA from Hu2, a second, but independent NIH3T3 focus transformant of the same derivation as Hu1; (j) DNA from the secondary tumor MCF-7-3-1; (k) DNA from the secondary tumor MCF-7-3-2. In this experiment, the amount of MCF-7 DNA loaded was proportionately less than the other lanes, as judged by ethidium bromide staining. Panel B: lanes a–i were as in Panel A; lanes j and k were DNAs from secondary tumors MCF-7-2-1 and MCF-7-2-2 respectively. The hybridizations were done at high stringency. Exposure times were 24 hours with intensifying screens. Numbers on right are DNA size markers in kbp.

DETAILS OF THE INVENTION

Plasmids bearing the following designations and deposit numbers are on deposit at the American Type Culture Collection, Bethesda, Md., and will be maintained and made available to the public according to the convention of the Budapest treaty:

| Plasmid | ATCC Number |
| --- | --- |
| mcf-2 | 40136 |
| mcf-3 | 40137 |

Preparation and Source of DNA

High molecular weight DNA from various cell lines was prepared as described previously (Perucho, M., et al. (1980) Cold Spring Harbor Symp. Quant. Biol. 45: 829–838). MCF-7 was from the Human Tumor Cell Line Bank of the Sloan Kettering Institute, Rye, N.Y. (Soule, H. D., et al. (1973) J. Natl. Cancer Inst. 51: 1409–1416). Preparation of DNA from solid tumors was done as follows: tumors (1–2 g frozen tissue) were finely ground by using a pestle in a mortar containing liquid $N_2$. The resulting powder was added to 40 ml of 400 mM NaCl, 10 mM EDTA, 20 mM Tris. HCl (pH 7.5), 0.5% SDS prewarmed at 68° C., and incubated at this temperature for 20 minutes. An additional incubation at 37° C. in the presence of poteinase K at the final concentration of 200 ug/ml was carried out with very slow agitation for 24–48 hours. Phenol extraction and subsequent steps were as described previously (Perucho, M., et al. (1981) Cell 27: 467–476). Plasmid and phage DNAs were prepared by published methods Kaiser, A. D., et al. (1960) J. Mol. Biol. 2: 392–415; Tanaka, T., et al. (1975) J. Bacteriol. 121: 354–362). Plasmids were used here obtained from other researchers are as follows: pKOneo, psrc 11, pBR Y73, pAB sub3, pGA-FeSV, pRCII-1B, pBR UR2, pAE PvuII, pHB-11, pKBE-2, pm-1, pMCV38, pVM-2, pFBJ-2, pSSV-11, pREV T3, pvski-1, pMT 2.5, pSM-FeSV, and blur 8, Phage myc4.1.1.

DNA Transfections and Nude Mice Assay

All DNA transfers used a modified calcium phosphate precipitation method (Gramham, F. L., et al. (1973) Virology, 52: 456–467; Wigler, M., et al. (1979) Cell 16: 777–785) using NIH3T3 cells as recipients (Jainchill, J. L., et al. (1969) J. Virol., 4: 549–553). Focus assays were performed as previously described (Perucho, M., et al. (1981) Supra). For the nude mouse experiments, 30 ug of cellular DNA plus 300 ng of pKOneo plasmid, were added as a calcium phosphate precipitate (volume 1 ml) to each 100 mm culture dish containing $5 \times 10^5$ cells in 10 ml of Dulbecco's medium and 10% calf serum (D10). After incubation for 8 hours, the precipitate was removed and replaced by 10 ml of fresh D10. After an additional 6 hours, each plate was trypsinized and seeded into four 10 mm dishes containing D10 plus 0.4 g/l of the antibiotic G418 (GIBCO) (as calculated for 100% active antibiotic). This time schedule is critical, since the antibiotic efficiently selects cells expressing the resistance marker only when seeding is done at low cell density. Refeeding of the cultures was done at intervals of three days using the same medium. The plates, each containing about 300 colonies, reached confluency after 16–18 days. At this time the four plates of cells were trypsinized, pooled, centrifuged at 700 rpm for 5 minutes and resuspended in 0.25 ml D10. Approximately $10^7$ cells were injected subcutaneously over the right shoulder of athymic, 4–8 weeks old male or female Nu-Nu mice of Rex-Trembler origin which had been back crossed to Swiss three times. One deviation from this protocol is described in the footnote to Table I.

Tumor growth was monitored weekly, and the mean diameter was calculated as the cubic root of the product of its three major diameters. Before death from tumor growth, the mice were sacrificed, and the tumor tissue (1-3 g) was frozen in liquid $N_2$ in order to obtain DNA at a later time.

Southern Filter Blot Hybridization

DNA samples were digested with restriction endonucleases and subjected to agarose gel electophoresis and filter-blot transfer by the method of Southern (Southern, E. M., et al. (1975) J. Mol. Biol. 98: 503-517). Filter-blotted DNAs were hybridized with nick-translated probes (Maniatis, T., et al. (1975) Proc. Natl. Acad. Sci. USA 72: 1184-1188) under stringent conditions described previously (Shimizu, K., et al. Proc. Natl. Acad. Sci, USA 80: 2112-2116). Nonstringent hybridization conditions entailed use of essentially the same components at 60° C. instead of 74° C. When total human or mouse DNA was nick translated and used as a probe, its concentration during hybridization was 0.03 mg/ml. For hybridization with ras probes, these DNAs: were nick translated plasmid p6aI, a partial cDNA clone of the human N-ras gene (Taparwosky, E., et al. (1983) Cell 34: 381-586); the 3.0 kbp EcoRI fragment containing coding exon II of the human K-ras gene (Shimizu, K., et al. (1983) Nature 304: 497-500); and the 0.7 kbp NarI/AvaI fragment from plasmid RS6 (Fasano, O., et al. (1983) J. Mol. Appl. Genetics 2: 173-180), a cDNA clone of the human H-ras gene containing most of the coding squences.

Isolation of mcf-1, -2 and -3

Genomic libraries of MCF-7 DNA and the secondary tumor DNAs (MCF-7-1-1, MCF-7-2-2 and MCF-7-3-4) were constructed in charon 4a (Blattner, F. R., et al. (1977) Science 196: 161-169; Hohn, B., et al. (1977) Proc. Natl. Acad. Sci USA 74: 3259-3263) from DNA partially digested with EcoRI restriction endonuclease and fractionated over sucrose gradient as described (Perucho, M., et al. (1981) Supra). To obtain clones of the mcf genes, $5 \times 10^5$ phages from libraries of secondary tumor DNAs were screened for human sequences by the method of Benton and Davis (Benton, W. D., et al. (1977) Science 196: 180-182) using nick-translated human placenta DNA as probes (Gusella, J. F., et al. (1980) Proc. Natl. Acad. Sci. USA 77: 2829-2833). To obtain mcf clones from MCF-7 DNA, that library was screened with repeat-free fragments of the respective genes. The filter hybridization was performed in $6 \times SSC$, $1 \times$ Denhardt at 68° C. for 20 hours followed by 5 washings in $2 \times SSC$ at 68° C.

Assays with MCF-7 DNA

In brief, the new assay was performed as follows: NIH3T3 cells were cotransfected with cellular DNA and DNA of the pKOneo plasmid, which renders animal cells resistant to the antibiotic G418 (Southern, P. J., et al. (1982) J. Mol. Appl. Genet. 1:327-341). In each experimental group, about $10^3$ G418 resistant colonies containing about $10^4$ cells were present after two to three weeks. These were pooled and injected into one nude mouse. The time of the first appearance of tumors and their subsequent growth was noted. As a positive control, one set of mice was inoculated with NIH3T3 cells exposed to genomic DNA from al-1, an NIH3T3 transformant containing a high copy number of the transforming human H-ras gene of T24 bladder carcinoma cells (Goldfarb, M., et al. (1982) Nature 296: 404-409; Perucho, M., et al. (1981) Cell 27: 467-476). As a negative control, one set of mice was inoculated with cells exposed to genomic DNA from NIH3T3 cells. Mice were maintained for up to 3 months. Positive results were obtained using MCF-7 DNA in the nude mouse assay (see Tables I and II). In two experiments, three independent tumors were obtained. There is a low tumor incidence in the negative control group (see Tables) as well as from mice injected with NIH3T3 cells exposed to human placental DNA. There is, therefore, a background of tumor induction when testing normal DNA. With MCF-7 DNA, as with many other tumor DNAs tumor incidence was higher than with control DNAs, but this may not be statistically signifiant. The assay is clearly responsive to high copies of strongly transforming genes since tumor incidence is markedly increased with the positive control groups consisting of nude mice injected with NIH3T3 exposed to DNA from al-1.

Tumors resulting from cells exposed to MCF-7 DNA were designated "primary tumors" MCF-7-1, MCF-7-2 and MCF-7-3. DNAs prepared from the primary tumors were used again in the tumorigenicity assay to obtain "secondary tumors". The lineages of the relevant tumors are given in Table III. In each case, DNA from the primary tumor was significantly more active at inducing tumorigenic NIH3T3 than the original MCF-7 DNA itself (see, for example, Table II). This probably results from the amplification of the transforming gene in primary transformants. Despite their higher activity in the nude mouse assay, DNA from primary tumors still cannot induce foci of morphologically altered NIH3T3. This reflects, an intrinsic difference between the present assay and the focus assay.

Figure 1:
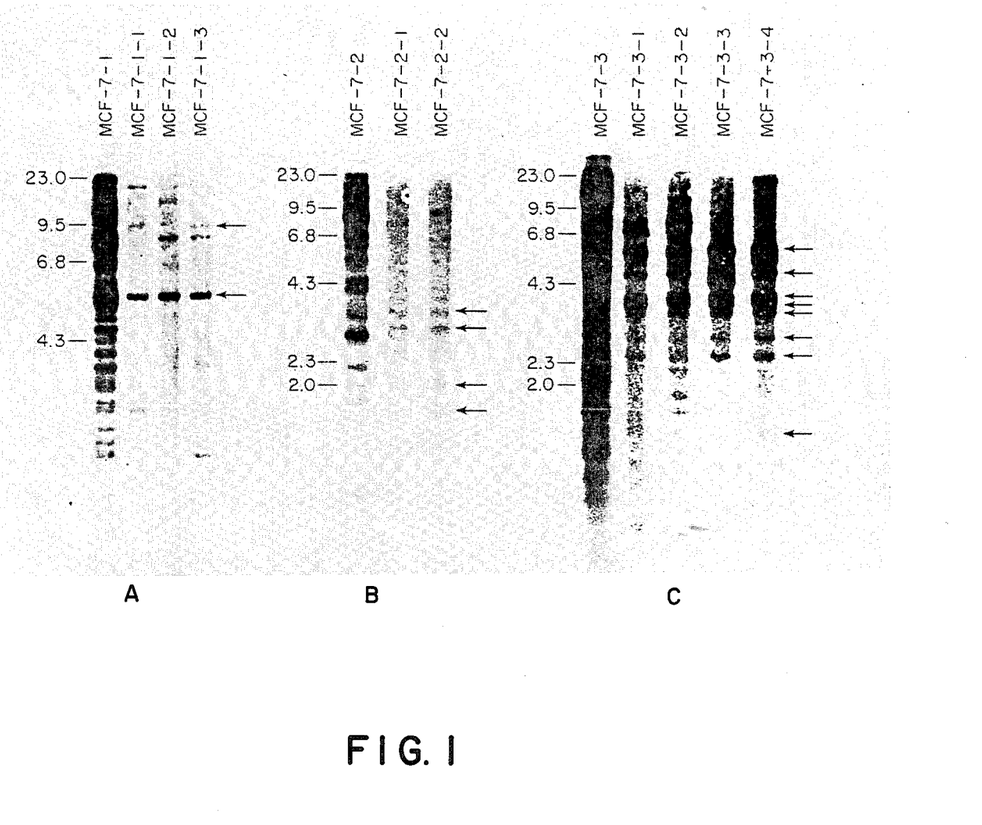

DNA from primary and secondary tumors were prepared and analysed by Southern blotting for the presence of human repetitive sequences (see FIG. 1). This powerful method allows the comparison of transforming genes prior to their actual isolation (Murray, M. J., et al. (1981) Cell 25: 355-361; Perucho, M., et al. (1981) Supra). All secondary tumors derived from the same primary tumor DNA contained a common set of human repetitive sequences. However, these sets differed between secondary tumors derived from different primary tumors DNAs. From this observation we conclude that the nude mouse assay appears to detect three different transforming genes in the DNA of MCF-7, which were designated mcf1, mcf2 and mcf3.

Relation of mcf Genes to the Known ras Genes

DNAs from the primary tumors were analysed for the presence of the three human ras genes, N-, H- and K-ras, by Southern analysis. Neither MCF-7-2 nor MCF-7-3 contained these genes. Later studies shouwed that indeed the mcf2 and mcf3 genes are not even weakly related to members of the ras gene family.

Figure 2:
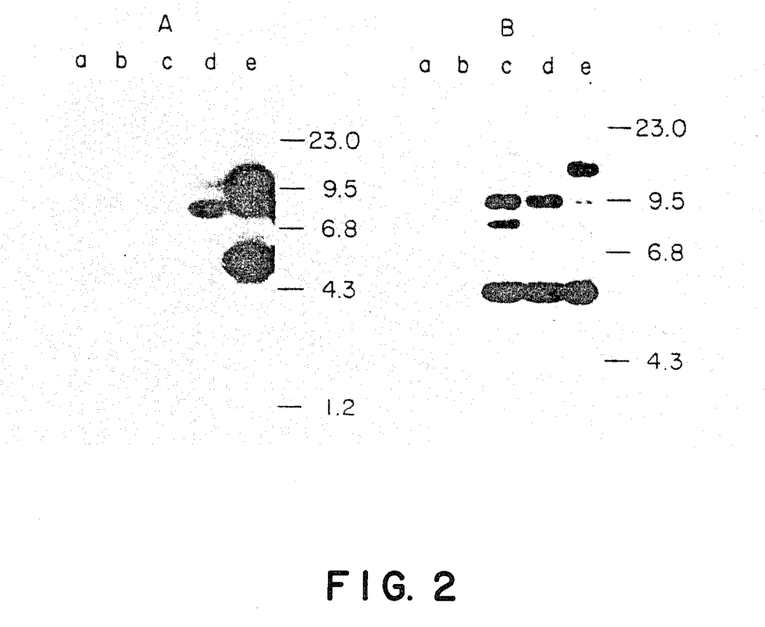

DNA from MCF-7-1, however, contained 30-100 copies of the human N-ras gene (see FIG. 2). Moreover, all secondary tumors derived from MCF-7-1 DNA contained a similar number of copies of the human N-ras gene. Therefore, mcf1 was N-ras. Although EcoR1 fragments with homology to N-ras are seen in the MCF-7-1 secondary DNAs, they are not the expected size. The N-ras gene from one of these DNAs, (MCF-7-1) was cloned, and its structure was analyzed. It contained the 9.2 kbp fragment, which corresponds to the intact 5' end of the N-ras gene (Taparowsky, E., et al. (1983) Cell 34: 581-586), but had undergone rearrangement in sequences which flanked the 3' end of the gene. To examine the possibility that the N-ras gene of MCF-7 was itself rearranged, southern blot analysis of MCF-7 DNA with an N-ras probe was performed. It was observed that this gene was not rearranged, at least within the 16.3 kbp region containing a functional N-ras gene. This was definitely established by the cloning of the N-ras region from MCF-7 DNA. It may be concluded that rearrangement of the N-ras gene in NIH3T3 transformants therefore occurred during or after gene transfer. Such rearrangements are common events during gene transfer (Goldfarb, M., et al. (1982) Nature 296-404-409; Pellicer, A., et al. (1978) Cell 1233-141).

These same studies however did indicate that the N-ras gene of MCF-7 is present at several times the copy number found in normal human diploid cells (see FIG. 2). These blot hybridization experiments were repeated several times with the same results. The amount of DNA loaded per slot was monitored by ethidium bromide staining and UV illumination of the agarose gel before DNA transfer onto nitrocellulose. After hybridizing nitrocellulose filters with nick translated N-ras probes and autoradiographic exposure, the amount of DNA transferred from gels by rehybridizing these filters was monitored with nick translated total human DNA and a second autoradiographic exposure. These studies indicated that N-ras was present in MCF-7 cells at 5 to 10 times the levels seen in cultured diploid human fibroblasts and human placenta.

Induction of Tumors with Ras Genes Encoding Normal Proteins

It was unexpectedly observed that DNA from MCF-7-1 could not induce morphologically altered foci in NIH3T3 cells. When the N-ras gene was cloned from a tumor induced by MCF-7-1 DNA, it too was unable to induce foci in NIH3T3 cells. Since the focus assay is sensitive to activated ras genes containing structural mutations. It was tentatively concluded that the N-ras gene of MCF-7 encodes anormal protein product, and, further, that the tumorigenicity assay, unlike the focus assay, is sensitive to cellular genes with the potential to induce tumorigenicity by increased expression of unaltered protein products.

To directly tested this hypothesis assays here performed of an activated H-ras gene cloned from T24 bladder carcinoma cells (Taparowsky, E., et al. (1982) Nature 300: 762-765), a wild type H-ras gene cloned from human placenta (Taparowsky, E., et al. (1982) Nature 300: 762-765), an activated N-ras gene cloned from SK-N-SH cells (Taparowsky, E., et al. (1983) Cell 34: 581-586), and a wild type N-ras gene cloned from human placenta (Taparowsky, E., et al. (1983) Cell 34: 581-586) (Table III). The results are summarized in Table IV. The structurally mutated, transforming H-ras and N-ras genes efficiently induced tumors. The H-ras and N-ras genes cloned from human placental DNA were much less active but did nevertheless efficiently induce tumors in nude mice. This may be attributed to the presence of multiple copies of these genes in NIH3T3 cells following DNA transfer, a hypothesis consistent with the work of others (Chang, E. H., et al. 91982) Nature 297: 479-483), who have shown that cells expressing high levels of the human H-ras gene product are tumorigenic.

It was still possible that the N-ras gene of MCF-7 contained mutations which made it more active in the tumorigenicity assay but not in the focus assay. However, the N-ras gene cloned from MCF-7-1-1 was no more efficient at inducing tumorigenicity than the N-ras gene cloned from human placental DNA (Table IV). A similar result was obtained when the N-ras gene cloned directly from MCF-7 DNA was assayed. These results suggest that the N-ras gene of MCF-7 does not contain significant structural mutations.

Preliminary Characterization of the mcf2 and mcf3 Genes

Figure 3:
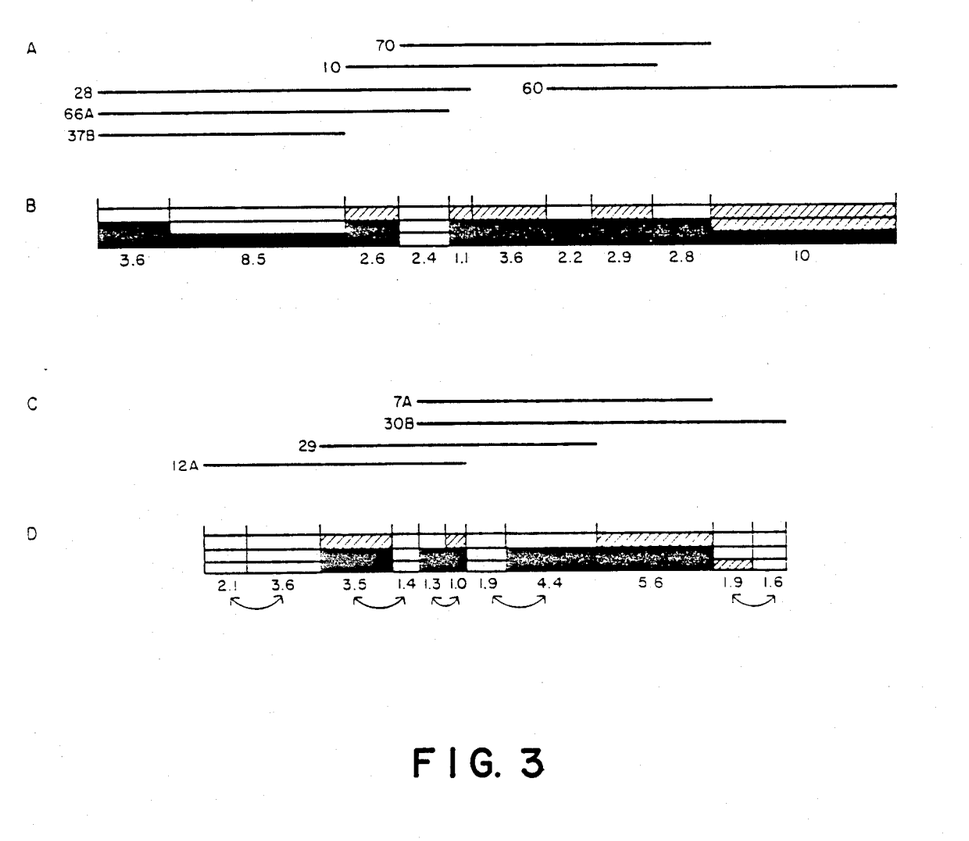
Figure 4:
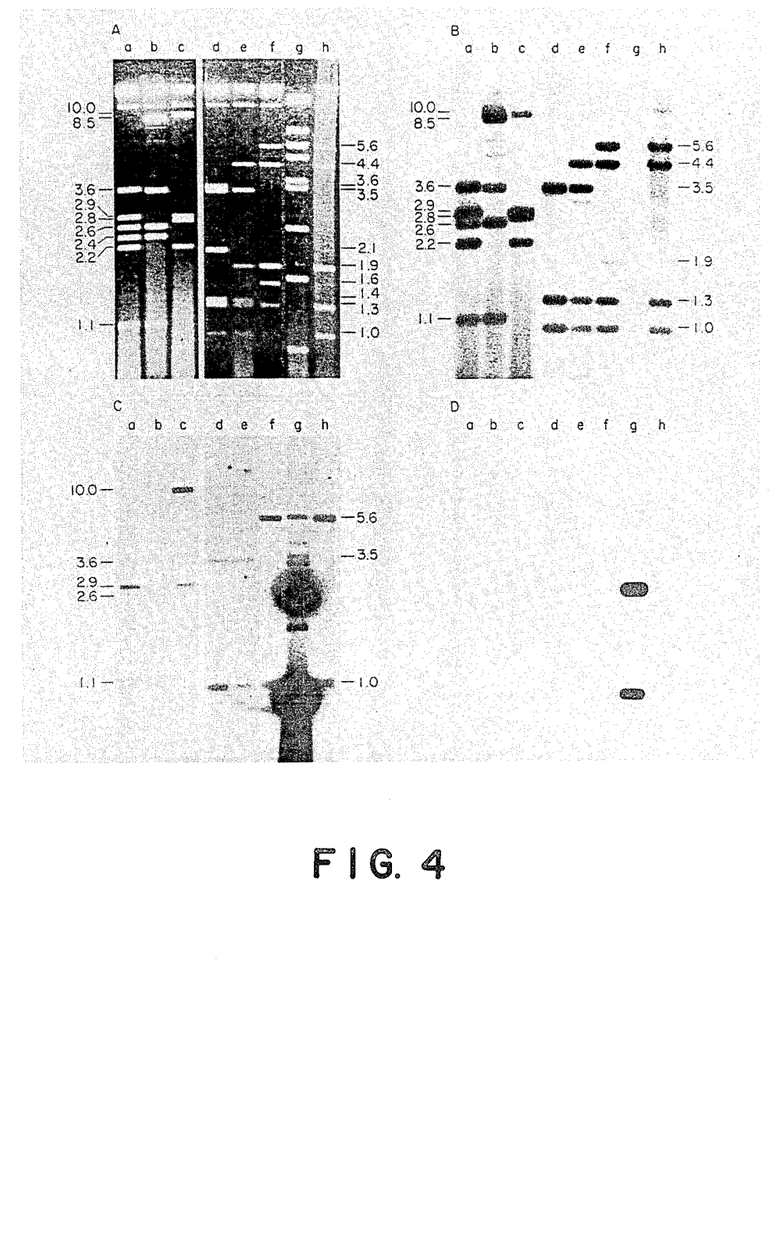

Portions of the two other genes detected by our assay of MCF-7 DNA were cloned. Using human repetitive sequences to isolate these genes from phage libraries were constructed using DNA from secondary tumors MCF-7-2 and MCF-7-3-4. In retrospect, this isolation was greatly facilitated by the high copy number of these genes present in induced mouse tumors (see FIG. 5). From overlapping phage inserts preliminary EcoR1 maps of these genes were determined (FIG. 3). The presence of mouse or human repeat sequences on these genes was also determined (FIGS. 3 and 4). None of the clones has shown strong hybridization to total nick translated mouse DNA (FIG. 4, panel D), but weak hybridization is observed between some fragments and mouse DNA on long autoradiographic exposures (FIG. 4, panel C). This maybe attributed to weak homology between humand and mouse sequences since sequences which were cloned directly from the human cell line MCF-7 also show this weak hybridization (see FIG. 4, lane h). However, the human DNA which we have isolated may contain rearrangements. Since none of the phage clones is biologically active in the nude mouse assay, these genes may be too large to clone in a biologically active form as a phage insert, and cosmid clones are being isolated.

Figure 5:
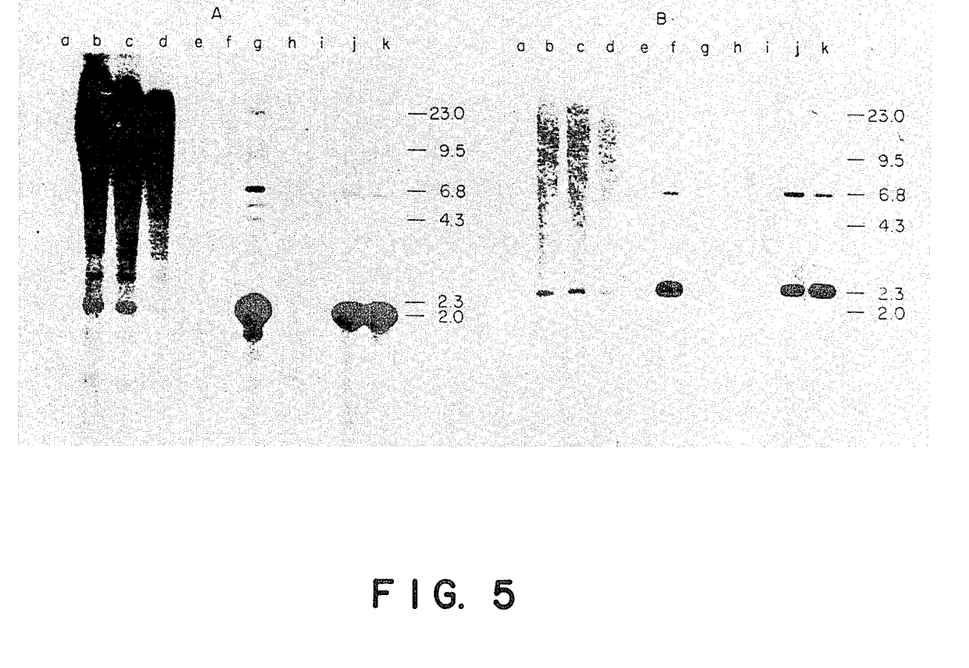

By blotting the cloned DNAs with total human or mouse DNA relatively repeat-free restriction endonuclease fragments useful for southern hybridization to genomic DNAs are identified. The copy number of these genes was examined in various transformants, in MCF-7 cells themselves and in transformed NIH3T3 cells obtained using MCF-7 DNA in a focus assay (FIG. 5). Evidently, mcf2 and mcf3 genes are not related to each other. They are present in high copy numbers in the primary tumors MCF-7-2 and MCF-7-3, respectively, and in the respective secondary tumors derived from them. However, neither gene appears to be amplified in MCF-7 DNA itself.

Finally, the cloned DNA was used as probes to search for homology to known oncogenes. This was done by low strigency blot hybridization to complete or nearly complete oncogene clones. For probes, a total of 39.7 kbp and 28.3 kbp from mcf2 and mcf3, respectively were nick transtated. No homology was seen to the clones of oncogenes shown in Table V (blot data not shown). Since this survey includes most of the known cellular oncogenes, it is apparent that mcf2 and mcf3 are previously uncharacterized transforming genes.

TABLE I

Tumorigenicity Assay of MCF-7 DNA[a]

| Donor DNA | Group | Day 14 | Day 21 | Day 28 | Day 35 | Day 42 | Day 49 | Day 56 | Day 63 | Tumor Designation |
|---|---|---|---|---|---|---|---|---|---|---|
| NIH3T3 | A | 0 | 0 | 0 | 0 | Trace | 14.5 | 17.0 | 20.0 | |
| | | 0 | 0 | 0 | 0 | Trace | 6.8 | 3.4 | 0 | |
| | | 0 | 0 | 0 | 0 | Trace | 6.6 | 0 | 0 | |
| MCF-7 | B | 0 | 9.1 | 18.8 | 23.3 | | | | | MCF-7-1a |
| | | 0 | Trace | 14.6 | 22.3 | | | | | MCF-7-1b |
| | | 0 | Trace | 12.2 | 21.5 | | | | | MCF-7-1c |
| | | 0 | Trace | 8.4 | 9.2 | 18.4 | | | | MCF-7-1d |
| | | 0 | Trace | 13.6 | 18.3 | | | | | MCF-7-1e |
| | | 0 | Trace | 9.0 | 16.7 | | | | | MCF-7-1f |
| | | 0 | Trace | 6.6 | 13.6 | | | | | MCF-7-1g |
| a1-1 | C | 21.9 | | | | | | | | |
| | | 20.2 | | | | | | | | |
| | | 15.1 | | | | | | | | |

[a]Tumorigenesis assays were performed essentially as described in the text. NIH3T3 cells were exposed to both pKOneo and DNA from the indicated cell line, and then selected for G418 resistance. Two weeks later, plates of surviving colonies were trypsinized, pooled, and injected into animals. Each group represents a pool of G418 resistant cells. Each line represents a single nude mouse injected with approximately $5 \times 10^6$ cells from the equivalent of four plates. Numbers in the table are mean tumor diameter in millimeters. a1-1 is an NIH3T3 transformant with a high copy number of a transforming H-ras gene (14,32). MCF-7 is a human breast cancer cell line (44). Tumors designated MCF-7-1a through MCF-7-1g all derived from the same initial transformed NIH3T3 cell since they display identical Southern blot patterns when probed from human repeat sequences (data not shown). This is consistent with their origin from a single pool of transformants. These tumors are referred to collectively as MCF-7-1. In subsequent experiments, we avoided this problem by injecting each mouse with an independent pool of transformed cells. See text for more details.

TABLE II[a]

Tumorigenicity Assay of MCF-7 and Primary Tumor DNAs

| Donor DNA | Group | Day 13 | Day 20 | Day 27 | Day 34 | Day 41 | Day 48 | Day 55 | Day 61 | Tumor Designation |
|---|---|---|---|---|---|---|---|---|---|---|
| NIH3T3 | A1 | 0 | 0 | 0 | 0 | 0 | 0 | 0 | 0 | |
| | A2 | 0 | 0 | 0 | 0 | 0 | 0 | 0 | 0 | |
| | A3 | 0 | 0 | 0 | 0 | 0 | 0 | 0 | 0 | |
| | A4 | 0 | 0 | 0 | 0 | 0 | 0 | 0 | 0 | |
| | A5 | 0 | 0 | 0 | 0 | 0 | 0 | 0 | 0 | |
| | A6 | 0 | 0 | 0 | 0 | 0 | 0 | 0 | 0 | |
| | A7 | 0 | 0 | 0 | 0 | 0 | 0 | 0 | 0 | |
| MCF-7 | B1 | 0 | 0 | 0 | 0 | 0 | 0 | 0 | 0 | |
| | B2 | 0 | 0 | 0 | 0 | 0 | 0 | 0 | 0 | |
| | B3 | 0 | 0 | Trace | 9.7 | 12.1 | 15.4 | | | MCF-7-2 |
| | B4 | 0 | 0 | 0 | 0 | 0 | 0 | 0 | 0 | |
| | B5 | 0 | 0 | 0 | 0 | 0 | 0 | 0 | 0 | |
| | B6 | 0 | 0 | 0 | 0 | 0 | 0 | 0 | 0 | |
| | B7 | 0 | 0 | 0 | Trace | 14.7 | 22.4 | | | MCF-7-3 |
| MCF-7-1 | C1 | 0 | 0 | 0 | Trace | 6.3 | 10.6 | 18.6 | | MCF-7-1-2 |
| | C2 | 0 | 0 | 0 | 0 | 0 | Trace | 6.6 | 12.1 | MCF-7-1-7 |
| | C3 | 0 | 0 | 0 | 0 | Trace | 8.1 | 15.4 | | MCF-7-1-3 |
| | C4 | 0 | 0 | 0 | 5.1 | 11.0 | 17.2 | | | MCF-7-1-1 |
| | C5 | 0 | 0 | 0 | 0 | 0 | 5.8 | 10.4 | 9.6 | MCF-7-1-5 |
| | C6 | 0 | 0 | 0 | 0 | Trace | 7.9 | 16.5 | — | MCF-7-1-4 |
| | C7 | 0 | 0 | 0 | 0 | 0 | 4.5 | 7.4 | 12.5 | MCF-7-1-6 |
| a1-1 | D1 | 14.4 | 22.8 | | | | | | | |
| | D2 | 10.2 | 20.8 | | | | | | | |
| | D3 | 13.1 | 25.9 | | | | | | | |

[a]See Table I and text. Each group represents an independent pool of transformants and each line a nude mouse inoculated with approximately $10^7$ cells.

TABLE III

Lineages of Tumors Grown in Nude Mice[a]

| Tumor designation | Induced by DNA from |
|---|---|
| MCF-7-1 | MCF-7 |
| MCF-7-1-1 | MCF-7-1 |
| MCF-7-1-2 | MCF-7-1 |
| MCF-7-1-3 | MCF-7-1 |
| MCF-7-2 | MCF-7 |
| MCF-7-2-1 | MCF-7-2 |
| MCF-7-2-2 | MCF-7-2 |
| MCF-7-3 | MCF-7 |
| MCF-7-3-1 | MCF-7-3 |
| MCF-7-3-2 | MCF-7-3 |
| MCF-7-3-4 | MCF-7-3 |

[a]The tumors to which we refer by name in the text are listed above, together with the cell or tumor DNA which was used to induce them.

TABLE IV

Tumorigenicity Assays of Normal and Mutant ras Genes[a]

| Donor DNA | Group | Day 7 | Day 14 | Day 21 | Day 28 | Day 35 | Day 43 | Day 50 |
|---|---|---|---|---|---|---|---|---|
| NIH3T3 | A1 | 0 | 0 | 0 | 0 | 0 | 0 | 0 |
| | A2 | 0 | 0 | 0 | 0 | 0 | 0 | 0 |

TABLE IV-continued

Tumorigenicity Assays of Normal and Mutant ras Genes[a]

| Donor DNA | Group | Day 7 | Day 14 | Day 21 | Day 28 | Day 35 | Day 43 | Day 50 |
|---|---|---|---|---|---|---|---|---|
| | A3 | 0 | 0 | 0 | 0 | 0 | 0 | 0 |
| NIH3T3 + H-ras pT24 | B1 | 7.8 | 21.5 | | | | | |
| 10 ng | B2 | 7.3 | 18.7 | | | | | |
| | B3 | 8.4 | 22.8 | | | | | |
| NIH3T3 + H-ras pP3 | C1 | 0 | 0 | 0 | 4.9 | 12.4 | 19.5 | 20.8 |
| 10 ng | C2 | 0 | 0 | 0 | 0 | 0 | 8.4 | 16.5 |
| | C3 | 0 | 0 | 0 | 4.5 | 11.4 | 18.8 | 19.5 |
| NIH3T3 + H-ras pP3 | D1 | 0 | 4.2 | 13.2 | 17.7 | | | |
| 100 ng | D2 | 0 | 4.9 | 14.3 | 20.8 | | | |
| | D3 | 0 | 5.3 | 8.9 | 16.5 | | | |
| NIH3T3 + N-ras λNS-35 | E1 | 7.3 | 27.3 | | | | | |
| 10 ng | E2 | 5.6 | 23.2 | | | | | |
| | E3 | 6.8 | 20.8 | | | | | |
| | E4 | 6.5 | 22.8 | | | | | |
| NIH3T3 + N-ras λNP-12 | F1 | 0 | 0 | 0 | 0 | 0 | 0 | 8.4 |
| 10 ng | F2 | 0 | 0 | 0 | Trace | 5.1 | 12.0 | 15.3 |
| | F3 | 0 | 0 | 0 | 6.2 | 10.2 | 15.8 | 20.3 |
| | F4 | 0 | 0 | 0 | 0 | 0 | 0 | 0 |
| NIH3T3 + N-ras λNP-12 | G1 | 0 | 0 | 0 | 9.6 | 15.3 | | |
| 100 ng | G2 | 0 | 0 | 5.7 | 11.6 | 20.7 | | |
| | G3 | 0 | 0 | 5.8 | 11.2 | 20.0 | | |
| | G4 | 0 | 0 | 3.9 | 8.9 | 15.6 | | |
| NIH3T3 + N-ras λMN-317 | H1 | 0 | 0 | 0 | 0 | 0 | 0 | 0 |
| 10 ng | H2 | 0 | 0 | 0 | 0 | 0 | 0 | 0 |
| | H3 | 0 | 0 | 0 | 0 | 0 | 4.0 | 8.4 |
| | H4 | 0 | 0 | 0 | 0 | 0 | 7.9 | 18.1 |
| NIH3T3 + N-ras λMN-317 | J1 | 0 | 0 | 0 | 8.4 | 16.5 | 24.6 | |
| 100 ng | J2 | 0 | 0 | 0 | 7.6 | 12.5 | 20.8 | |
| | J3 | 0 | 0 | 0 | Trace | 7.2 | 15.8 | |
| | J4 | 0 | 0 | 0 | 8.4 | 15.3 | 20.5 | |
| a1-1 | K | 10.4 | 18.7 | | | | | |

[a]In this experiment each plate of NIH3T3 cells was exposed to the usual concentration of pKOneo and 30 μg of NIH3T3 DNA (groups A-J) or a1-1 DNA (group K). Moreover, each plate (groups B-J) received the following additions: group B, 10 ng of the transforming human H-ras gene cloned from T24 DNA, called plasmid pT24; group C and D, 10 ng and 100 ng, respectively, of the wild-type H-ras gene cloned from human placental DNA, called plasmid pP3; group E, 10 ng of the transforming human N-ras gene cloned from SK-N-SH neuroblastoma cells, called λNS-35; group F and G, 10 ng and 100 ng, respectively, of the wild-type N-ras gene cloned from human placental DNA, called λNP-12; group H and J, 10 ng and 100 ng, respectively, of the human N-ras gene cloned from MCF-7-1-1, called λMN-317.

TABLE V

Molecular Clones of Oncogenes

| Designation and origin | | Clone | Reference |
|---|---|---|---|
| abl | Abelson murine leukemia virus | pAB sub3 | Goff et al., (1980) Cell 22:777–785 |
| erb | avian erythroblastosis virus | pAE PvnII | Vennstrom et al., (1980) J. Virol. 36:575–585 |
| fes | GA feline sarcoma virus | pGA-FeSV | Fedele et al., (1981) Proc. Natl. Acad. Sci. 78:4036–4040 |
| fos | FBJ osteosarcoma virus | pFBJ-2 | Curran et al., (1982) J. Virol. 44:674–682 |
| fms | SM feline sarcoma virus | pSN-FeSV | Donner et al., (1982) J. Virol. 41:489–500 |
| fps | PRCII avian sarcoma virus | pRCII-1B | |
| H-ras | Harvey murine sarcoma virus | pHB-11 | Ellis et al., (1981) Nature 292:506–511 |
| int-1 | Mouse mammary carcinoma | pMT 2.5 | Nusse et al. (1984) Nature 307:131–136 |
| K-ras | Kirsten murine sarcoma virus | pKBE-2 | Ellis et al., (1981) Nature 292:506–511 |
| mos | Moloney murine sarcoma virus | pm-1 | Blair et al., (1980) Proc. Natl. Acad. Sci. 77:3504–3508 |
| myb | Avian myeloblastosis virus | pVH-2 | Klempnauer et al., (1983) Cell 33:345–355 |
| myc | Avian Myelocytomatosis | pMCV38 | Vennstrom et al., (1981) J. Virol. 39:625–631 |
| N-ras | Human Neuroblastoma | p6aI | Taparowsky et al., (1983) Cell 34:581–586 |
| rel | Reticuloendotheliosis virus | pRev T3 | Cehn and Temin (1982) Cell 31:111–120 |
| ros | UR2 avian sarcoma virus | pBR UR2 | |
| sis | Simian sarcoma virus | pSSV-11 | Robbins et al., (1982) Science 218:1131–113 |
| ski | Avian SKV770 virus | pvski-1 | Stavnezer, E., et al. (1981) J. Virol. 39:920–934. |

TABLE V-continued

Molecular Clones of Oncogenes

| Designation and origin | | Clone | Reference |
|---|---|---|---|
| src | Rous sarcoma virus | psrc 11 | Shalloway et al., (1981) Cell 24:531–541 |
| yes | Y73 sarcoma virus | pBR Y73 | Kitamura et al., (1982) Nature 297:205 208 |

What is claimed:

1. The transforming gene contained in the plasmid having the American Type Culture Collection reference number 40136.

2. The transforming gene contained in the plasmid having the American Type Culture Collection reference number 40137.

* * * * *

UNITED STATES PATENT AND TRADEMARK OFFICE
CERTIFICATE OF CORRECTION

PATENT NO. : 4,866,166

DATED : September 12, 1989

INVENTOR(S) : Michael H. Wigler, Daniel Birnbaum, Carmen Birchmaier and Ottavio Fasano It is certified that error appears in the above-identified patent and that said Letters Patent is hereby corrected as shown below:

In the title page adjacent to "[75]", delete "Inventor: Michael Wigler, Osterhout, N.Y.", and insert --Inventors: Michael H. Wigler, Cold Spring Harbor, NY; Daniel Birnbaum, Marseilles, France; Carmen Birchmaier, Cold Spring Harbor, NY; and Ottavio Fasano, Heidelberg, West Germany--

Item [19] should read --Wigler, et al--

Signed and Sealed this

Eighteenth Day of June, 1991

*Attest:*

HARRY F. MANBECK, JR.

*Attesting Officer*         *Commissioner of Patents and Trademarks*